United States Patent [19]

François et al.

[11] Patent Number: 5,453,425
[45] Date of Patent: Sep. 26, 1995

[54] RISPERIDONE ORAL FORMULATION

[75] Inventors: Marc K. J. François, Brussel; Willy M. A. C. Dries, Merksplas, both of Belgium

[73] Assignee: Janssen Pharmaceutica N.V., Beerse, Belgium

[21] Appl. No.: 272,462

[22] Filed: Jul. 11, 1994

[51] Int. Cl.$^6$ ............................ A61K 9/08; A61K 31/505
[52] U.S. Cl. ................................................................ 514/258
[58] Field of Search ...................................... 514/258

[56] References Cited

U.S. PATENT DOCUMENTS 5,001,134  3/1991  Ferrand et al. ..................... 514/321
5,246,935  9/1993  Jeppesen et al. .................... 514/253

Primary Examiner—Shep K. Rose
Attorney, Agent, or Firm—Charles J. Metz

[57] ABSTRACT

The present invention is concerned with physicochemically stable aqueous solutions of risperidone for oral administration which do not contain sorbitol.

7 Claims, No Drawings

RISPERIDONE ORAL FORMULATION

The present invention is concerned with physicochemically stable aqueous solutions of risperidone for oral administration which do not contain sorbitol.

BACKGROUND OF THE INVENTION

EP-0,196,132 discloses an oral solution containing a 1,2-benzisoxazol-3-yl derivative, methylparaben, propylparaben, tartaric acid, Na-saccharin, raspberry and gooseberry essence, and the polyhydric alcohols sorbitol and glycerol (1,2,3-propanetriol). Comparable solutions wherein the benzisoxazole derivative was risperidone, however, were found to exhibit an unsatisfactory physicochemical stability. Unexpectedly, sorbitol was found to cause decomposition of risperidone upon storage of the solution at elevated temperatures, i.e. under conditions which imitate those of a long storage time. A physicochemically stable risperidone solution was obtained after omitting the sorbitol constituent from the composition.

DESCRIPTION OF THE INVENTION

The present invention concerns an aqueous solution for oral administration comprising water, risperidone or a pharmaceutically acceptable acid addition salt thereof, a buffer to maintain the pH in the range of 2 to 6, and a preservative, characterized in that said solution is essentially free of sorbitol.

The subject compositions are characterized by their improved physicochemical stability when compared to the art composition. The term "physicochemically stable" as herein defined refers to a solution wherein, after storage for a period up to 4 weeks at a temperature of 80° C. or below, the residual amount of risperidone is 80% or more of the initial risperidone concentration. Several compositions of the subject invention are characterized by an unchanged concentration of fispefidone under even more stringent conditions, in particular an extended storage time at an elevated temperature.

Hereinafter, the amounts of each of the ingredients in the compositions are expressed as percentages by weight based on the total volume of the formulation. Ratios are intended to define weight-by-weight ratios.

Risperidone is generic to 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one. The preparation and pharmacological activity thereof are described in EP-0,196,132. The term risperidone as used herein comprises the free base form and the pharmaceutically acceptable acid addition salts thereof. The solubility of risperidone is increased upon the formation of such salt forms, which can be obtained by reaction of the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids. The term addition salt as used hereinabove also comprises the solvates which risperidone as well as the salts thereof, are able to form. Such solvates are for example hydrates, alcoholates and the like.

The amount of risperidone in the present compositions ranges from 0.01% to 1%, preferably from 0.02% to 0.5%, most preferably from 0.05% to 0.2%, and in particular is 0.1%.

The oral solutions according to the present invention have a pH from 2 to 6, preferably from 3 to 5 and most preferably from 3 to 4. The pH of the composition may be maintained upon the addition of a buffer system. Buffer systems comprise mixtures of appropriate amounts of an acid such as phosphoric, succinic, tartaric, lactic, or citric acid, and a base, in particular sodium hydroxide or disodium hydrogen phosphate. The desired pH range is advantageously obtained using a tartaric acid / sodium hydroxide buffer.

In order to prevent the growth of micro-organisms such as bacteria, yeasts and fungi in the subject compositions, a preservative agent is added. Suitable preservatives should be physicochemically stable and effective in the pH range mentioned above. They comprise benzoic acid, sorbic acid, methylparaben, propylparaben, imidazolidinyl urea (=Germall 115®) and diazolidinyl urea (=Germall II®), phenoxetol, benzyl alcohol, quaternary compounds, e.g. benzylalkonium chloride, and the like. Some preservatives, such as benzoic acid, sorbic acid, Germall 115®, Germall II® and benzyl alcohol, have the advantage that they yield clear, transparant solutions which do not show any clouding upon storage. The concentration of the preservatives may range from 0.05% to 1%, particularly from 0.1% to 0.5%, and most particularly is about 0.2%. The most preferred preservative is benzoic acid.

The subject compositions optionally comprise further additives known in the art of formulation such as sweetening agents, flavouring substances, solubility enhancers, viscosity regulating agents and the like additives. For example, the aqueous solubility of the active ingredient may be enhanced by the addition of a pharmaceutically acceptable co-solvent, or a cyclodextrin or a derivative thereof, to the solution.

The bitter taste of risperidone and the unpleasant taste associated with the pH of some formulas may be masked by the presence of one or more sweetening agents such as saccharin, sodium, potassium, calcium saccharin, acesulfame potassium or sodium cyclamate. The concentration of the sweetening agent may range from 0.04% to 0.15% and in particular is about 0.1%. In a particular embodiment of the invention, the solution does not comprise polyhydric alcohols, e.g. mannitol, fructose, sucrose, maltose and the like, as sweetening agents. The palatability of the subject solutions may further be optimized by adding of one or more flavouring substances. Suitable flavouring substances are fruit flavours such as cherry, raspberry, black currant or strawberry flavour, or stronger flavours, such as Caramel Chocolate flavour, Mint Cool flavour, Fantasy flavour and the like. Combinations of flavours are advantageously used. A combination of two cherry flavours was found to yield very good taste masking results in the present compositions. The total concentration of the flavouring substances may range from 0.01% to 0.5%, preferably from 0.03% to 0.2% and most preferably from 0.05% to 0.1%.

The palatability of the solution and, hence, the patient compliance to the medication may further be increased by diluting the subject compositions with a beverage or drinking liquid such as coffee, tea, a soft drink and the like.

A particular composition according to the present invention comprises (a) 0.02% to 0.5% risperidone;
(b) 0.1% to 0.5% preservatives;

(c) a suitable amount of buffer to adjust the pH in the range from 2 to 6; and (d) water.

The most preferred composition according to the present invention contains (a) 0.1% risperidone;

(b) 0.2% benzoic acid;

(c) 0.75% tartaric acid and sufficient sodium hydroxide 1 N to adjust the pH in the range from 2 to 6; and (d) water q.s. ad 100%.

In a further aspect, the present invention relates to a process of preparing solutions of risperidone as described hereinabove, characterized by dissolving the active ingredient risperidone, the preservative, and the acid and base components of the buffer in water. In particular, the process comprises the following steps: (a) dissolving the preservative in an amount of heated water, (b) diluting the solution with about an equal amount of water, (c) adding the acid component of the buffer and the active ingredient risperidone thereto, (d) stirring the mixture until complete dissolution and cooling the solution to room temperature, (e) adjusting the pH with the base component of the buffer and further diluting the solution with water to the required end-volume. Optionally, one or more sweetening agents and flavouring substances may be added during these process steps.

The following examples are intended to illustrate the scope of the present invention in all its aspects but not to limit it thereto.

EXAMPLE 1

| F1: oral solution (pH = 3 ± 1) | |
| --- | --- |
| Ingredient | Quantity, mg/ml oral solution |
| risperidone | 2 |
| tartaric acid | 7.5 |
| benzoic acid | 2 |
| Cherry flavour 1 | 0.25 |
| Cherry flavour 2 | 0.5 |
| sodium saccharin | 1 |
| sodium hydroxide | 1 |
| purified water | q.s. ad 1 ml |

(1) 2 mg benzoic acid was dissolved in 0.5 ml water upon stirring at 80°–90° C. 0.4 ml water was added to the solution and 7.5 mg tartaric acid and 2 mg risperidone were dissolved in the resulting mixture upon stirring.

(2) 1 mg sodium saccharin was dissolved in 0.05 ml water upon stirring.

(3) fractions (1) and (2) were mixed upon stirring and the solution was cooled to room temperature.

(4) 0.25 mg Cherry flavour 1 and 0.5 mg Cherry flavour 2 were added to fraction (3) upon stirring.

(5) 1 mg sodium hydroxide was added to fraction (4) to adjust the pH to about 3.

(6) fraction (5) was further diluted with water to 1 ml. In a similar way there were prepared:

| Ingredient | Quantity, mg/ml oral solution |
| --- | --- |
| F2: oral solution (pH = 4 ± 1) | |
| risperidone | 0.5 |
| tartaric acid | 7.5 |
| benzoic acid | 2 |
| Cherry flavour 1 | 0.25 |
| Cherry flavour 2 | 0.5 |
| sodium saccharin | 1 |
| sodium hydroxide | q.s. pH = 4 ± 1 |
| purified water | q.s. ad 1 ml |
| F3: oral solution (pH = 3) | |
| risperidone | 0.5 |
| tartaric acid | 7.5 |
| sodium chloride | 5 |
| sodium saccharin | 1 |
| sodium hydroxide | q.s. pH = 3 |
| purified water | q.s. ad 1 ml |
| F4: oral solution (pH = 5) | |
| risperidone | 0.5 |
| tartaric acid | 7.5 |
| sodium chloride | 5 |
| sodium saccharin | 1 |
| sodium hydroxide | q.s. pH = 5 |
| purified water | q.s. ad 1 ml |
| F5: oral solution (pH = 3) | |
| risperidone | 1 |
| tartaric acid | 7.5 |
| benzoic acid | 2 |
| sodium hydroxide | 1 |
| purified water | q.s. ad 1 ml |

EXAMPLE 2

The tables hereinbelow summarize the risperidone concentrations measured after a particular storage time of the composition at a particular temperature, expressed as the percentage of the initial risperidone concentration.

TABLE 1

| | | | F1 | F2 |
| --- | --- | --- | --- | --- |
| 4° C. | 12 | months | 98.2 | |
| 25° C. | 1 | month | 100.4 | 101.1 |
| | 3 | months | 102.1 | 99.1 |
| | 6 | months | 100.9 | |
| | 9 | months | 99.5 | |
| | 12 | months | 98.7 | |
| 30° C. | 3 | months | 102.1 | 98.8 |
| | 6 | months | 100.3 | |
| | 12 | months | 98.9 | |
| 40° C. | 1 | month | 102.1 | 101.1 |
| | 3 | months | 100.9 | 99.4 |
| | 6 | months | 100.5 | |
| | 12 | months | 98.3 | |
| 60° C. | 1 | month | 100.1 | 100.3 |

TABLE 2

| | | F3 | F4 |
| --- | --- | --- | --- |
| 80° C. | 5 days | 97.9 | 99.0 |
| | 17 days | 96.7 | 96.6 |
| | 4 weeks | 86.2 | 87.6 |

The data in the tables indicate that compositions F1–F4 satisfy the criteria as set forth hereinbefore to qualify as a "physicochemically stable" composition.

We claim:

1. An aqueous solution for oral administration comprising water, risperidone or a pharmaceutically acceptable acid addition salt thereof, a buffer to maintain the pH in the range of 2 to 6, and a preservative, characterized in that said solution is essentially free of sorbitol.

2. A solution according to claim 1 having a pH ranging from 3 to 4.

3. A solution according to claim 2 wherein said pH range is obtained with a tartaric acid /sodium hydroxide buffer.

4. A solution according to claim 1 wherein the amount of risperidone ranges from 0.01% to 1% by weight based on the total volume of the solution.

5. A solution according to claim 1 wherein the preservative is benzoic acid.

6. A solution according to claim 1 containing
   (a) 0.1% risperidone;
   (b) 0.2% benzoic acid;
   (c) 0.75% tartaric acid and sufficient sodium hydroxide 1N to adjust the pH in the range from 2 to 6; and
   (d) water q.s. ad 100%.

7. A solution according to claim 1 further comprising one or more sweetening agents and/or flavouring substances.

* * * * *